(12) United States Patent
Forsell

(10) Patent No.: US 11,382,640 B2
(45) Date of Patent: Jul. 12, 2022

(54) MEDICAL DEVICE AND METHOD FOR TREATMENT OF HIP JOINT

(71) Applicant: Peter Forsell, Bouveret (CH)

(72) Inventor: Peter Forsell, Bouveret (CH)

(*) Notice: Subject to any disclaimer, the term of this patent is extended or adjusted under 35 U.S.C. 154(b) by 482 days.

(21) Appl. No.: 15/670,061

(22) Filed: Aug. 7, 2017

(65) Prior Publication Data
US 2017/0333054 A1 Nov. 23, 2017

Related U.S. Application Data

(63) Continuation of application No. 13/383,039, filed as application No. PCT/SE2010/050815 on Jul. 12, 2010, now Pat. No. 9,724,200.
(Continued)

(51) Int. Cl.
*A61B 17/16* (2006.01)
*A61F 2/36* (2006.01)
(Continued)

(52) U.S. Cl.
CPC ...... *A61B 17/1666* (2013.01); *A61B 17/1617* (2013.01); *A61B 17/1668* (2013.01);
(Continued)

(58) Field of Classification Search
CPC ............ A61B 17/1664; A61B 17/1666; A61B 17/1668
See application file for complete search history.

(56) References Cited

U.S. PATENT DOCUMENTS

2008/0183174 A1* 7/2008 Sikora ................ A61B 17/1617 606/83

* cited by examiner

*Primary Examiner* — Olivia C Chang

(57) ABSTRACT

A medical device for delivering an action to an area of a hip joint or its surroundings, inside a human body of a patient, the hip joint comprising a collum femur and a ball shaped caput femur, being the proximal parts of the femoral bone, and an acetabulum, being a bowl shaped part of the pelvic bone, said medical device comprising an elongated member, having a length axis along its elongated distribution, and a first portion having an end being adapted to enter the body of the patient, said first portion of said elongated member having a first portion cross-section area substantially perpendicular to the length axis of the elongated member, said first portion is adapted to pass through a hole in a bone of the patient, the hole having a hole cross-section area, wherein said first portion cross-section area is smaller than said hole cross-section area, the first portion comprising a mounting portion, and a holding member adapted to hold a mechanical element inside the body of said patient, and a mechanical element having a functional status ready to deliver an action inside the body when held by said holding member inside the body of the patient, wherein said mechanical element has a mechanical element cross-section area substantially perpendicular to the length axis of the elongated member, being substantially larger than said first portion cross-section area and unable to pass through the holes when said mechanical element is in said functional status, characterized in that the mechanical element comprises at least one mounting recess for mounting the mechanical element onto the mounting portion of the elongated member in a direction substantially perpendicular to the elongated member, such that a user of the medical device can mount the mechanical element on the elongated member without having access to the end of the first portion of the elongated member, wherein said mechanical element is adapted to be used during an operation in the hip joint or its surroundings, when placed inside the body.

20 Claims, 16 Drawing Sheets

Related U.S. Application Data

(60) Provisional application No. 61/229,752, filed on Jul. 30, 2009, provisional application No. 61/229,778, filed on Jul. 30, 2009, provisional application No. 61/229,743, filed on Jul. 30, 2009, provisional application No. 61/229,738, filed on Jul. 30, 2009, provisional application No. 61/229,745, filed on Jul. 30, 2009, provisional application No. 61/229,751, filed on Jul. 30, 2009, provisional application No. 61/229,796, filed on Jul. 30, 2009, provisional application No. 61/229,786, filed on Jul. 30, 2009, provisional application No. 61/229,739, filed on Jul. 30, 2009, provisional application No. 61/229,747, filed on Jul. 30, 2009, provisional application No. 61/229,735, filed on Jul. 30, 2009, provisional application No. 61/229,761, filed on Jul. 30, 2009, provisional application No. 61/229,789, filed on Jul. 30, 2009, provisional application No. 61/229,755, filed on Jul. 30, 2009, provisional application No. 61/229,746, filed on Jul. 30, 2009, provisional application No. 61/229,767, filed on Jul. 30, 2009, provisional application No. 61/229,748, filed on Jul. 30, 2009, provisional application No. 61/213,814, filed on Jul. 17, 2009.

(51) Int. Cl.
 *A61F 2/32* (2006.01)
 *A61F 2/30* (2006.01)

(52) U.S. Cl.
 CPC .............. *A61F 2/32* (2013.01); *A61F 2/3603* (2013.01); *A61F 2002/305* (2013.01); *A61F 2002/30469* (2013.01); *A61F 2002/30471* (2013.01); *A61F 2002/30495* (2013.01); *A61F 2002/30594* (2013.01); *A61F 2002/30616* (2013.01); *A61F 2002/30818* (2013.01); *A61F 2220/0025* (2013.01)

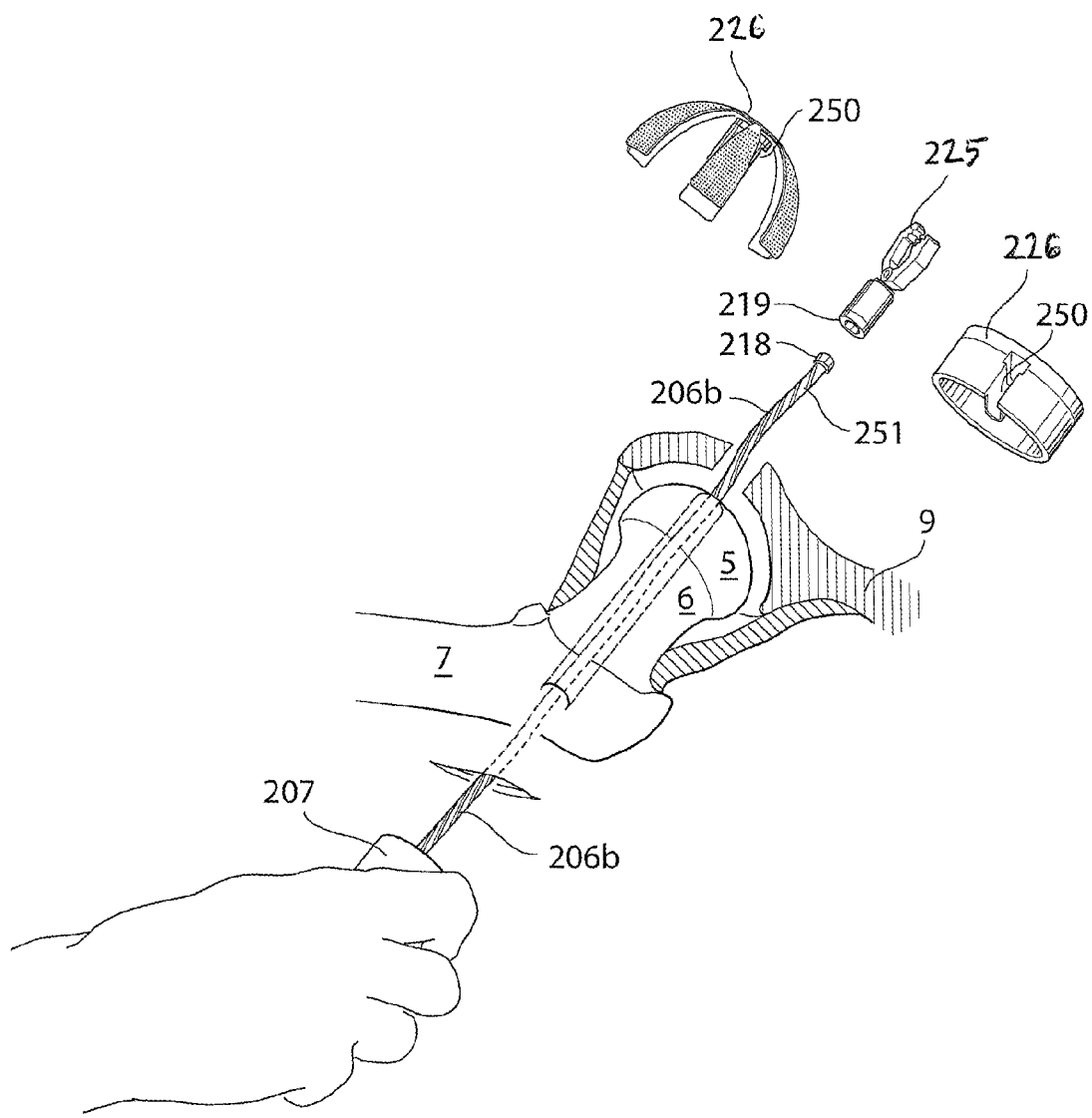

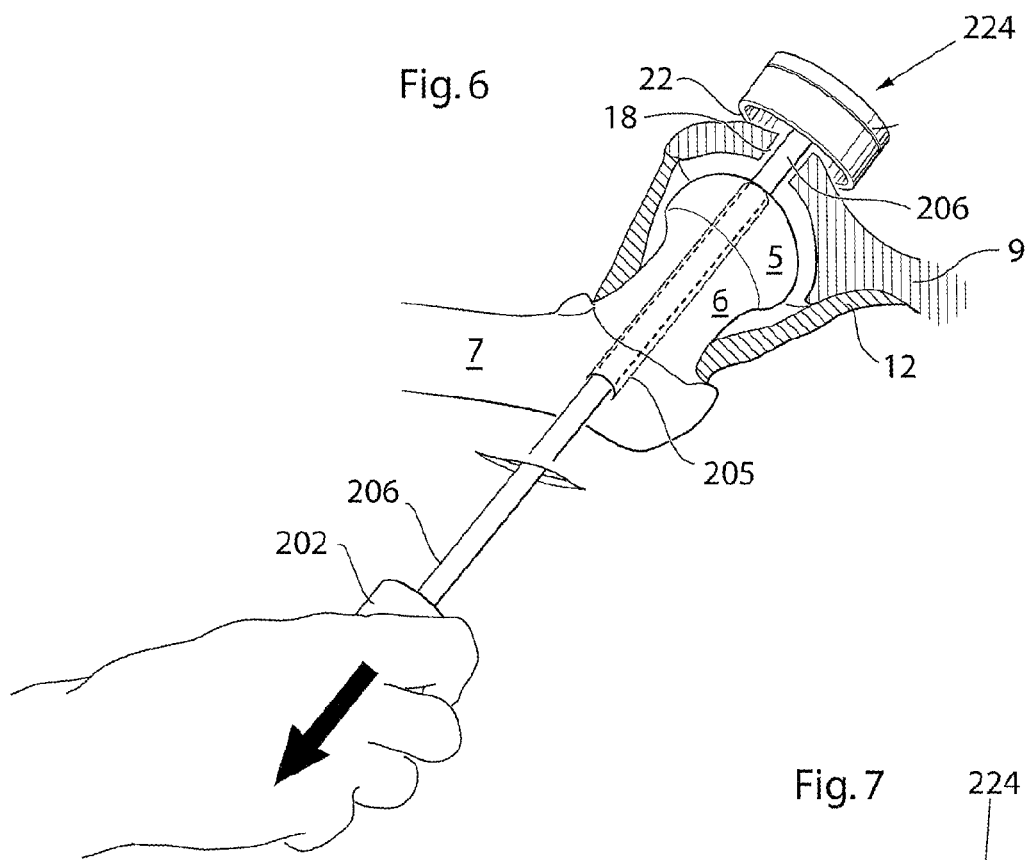
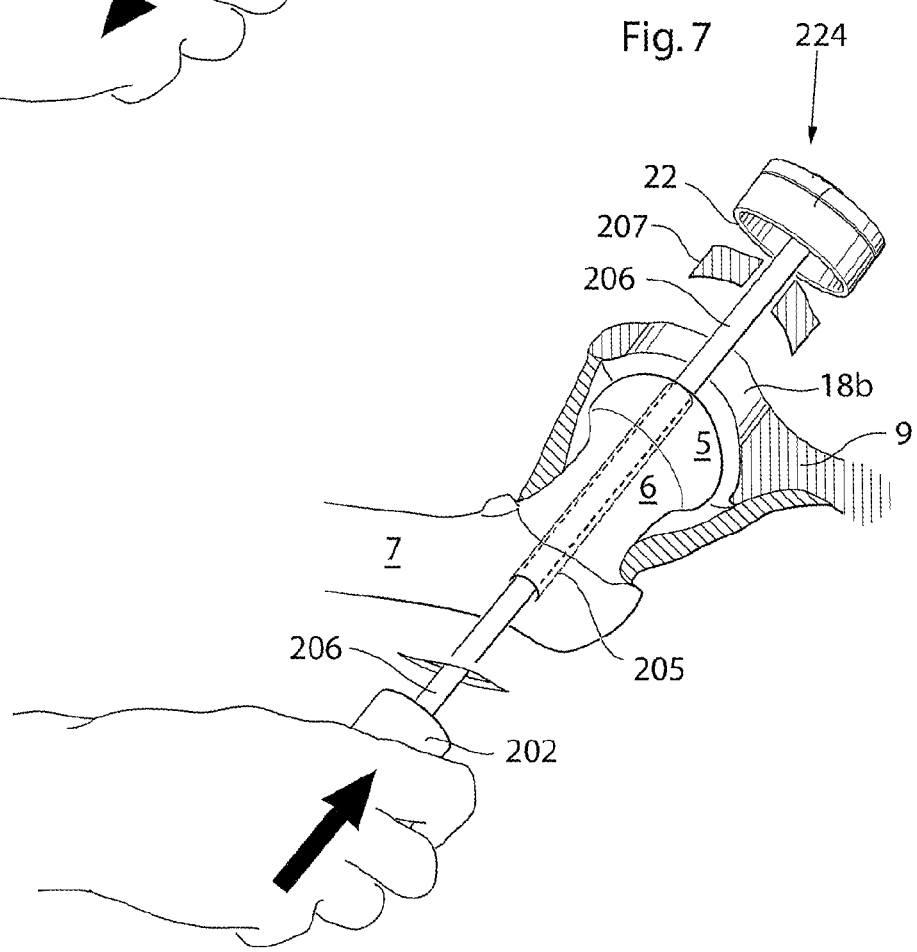

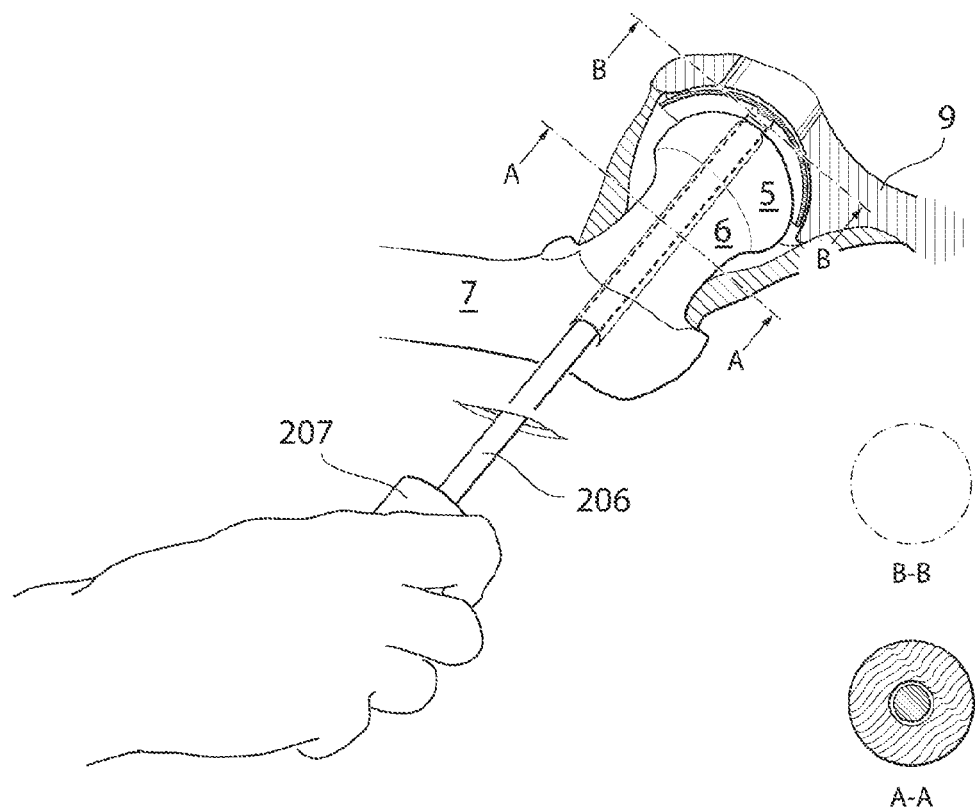

Fig. 11e
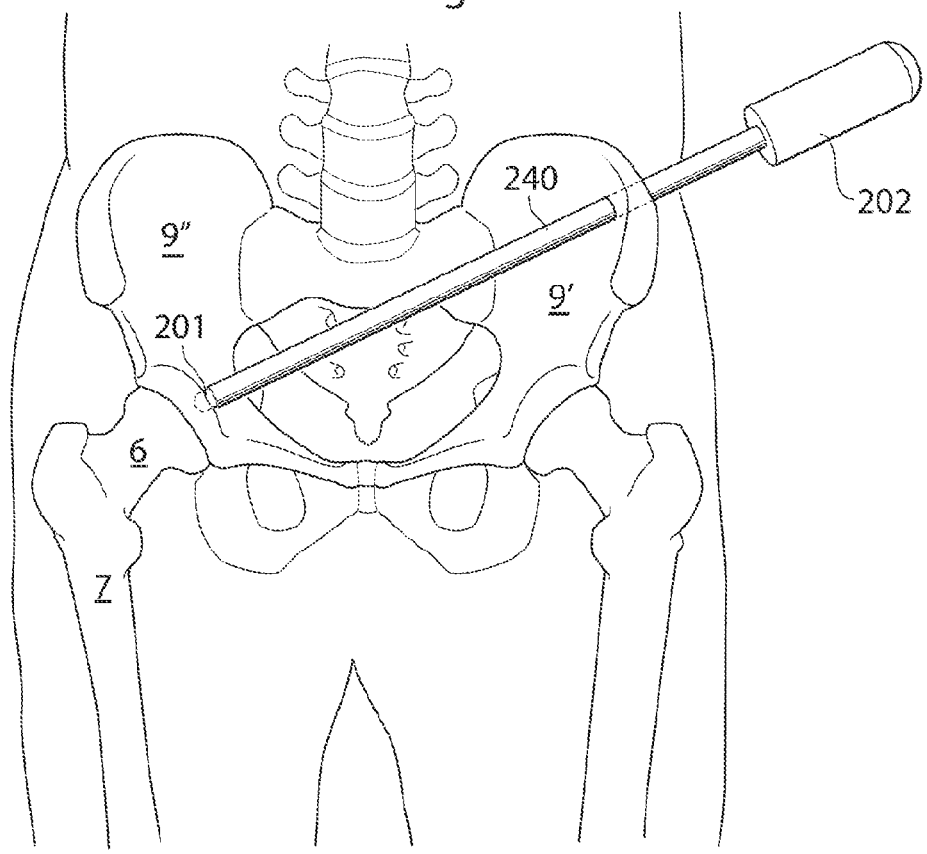
Fig. 11f
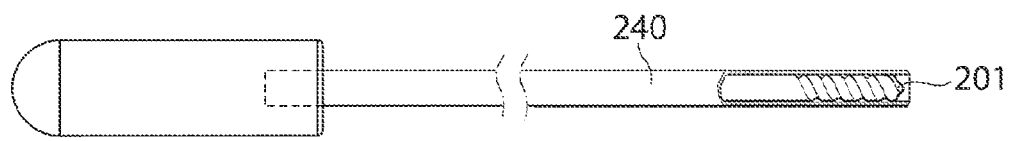
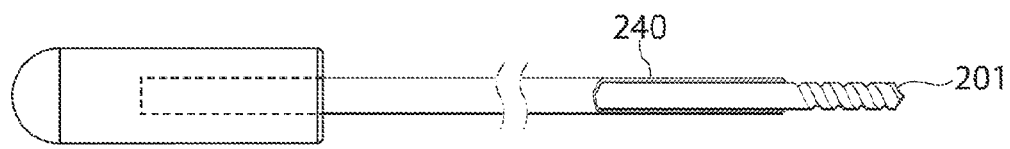

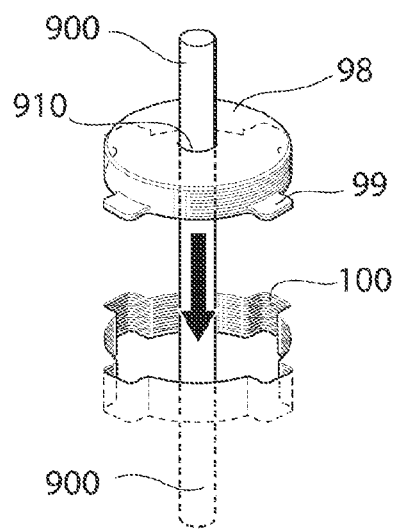
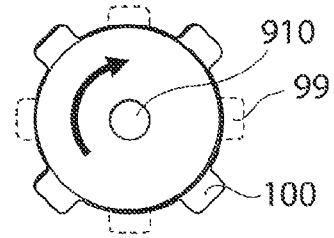
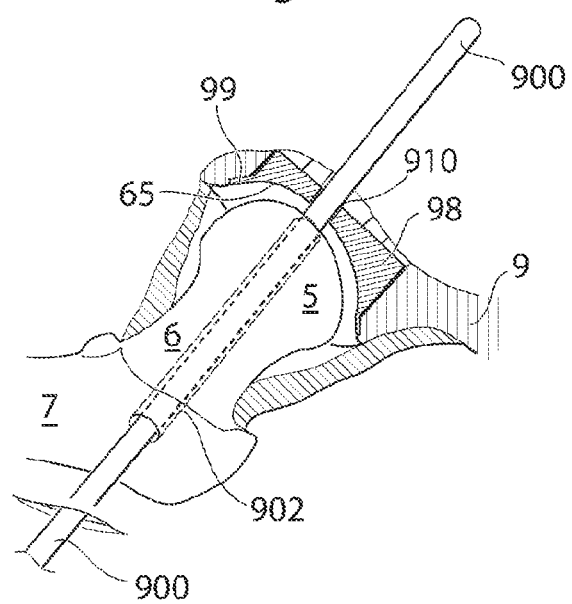

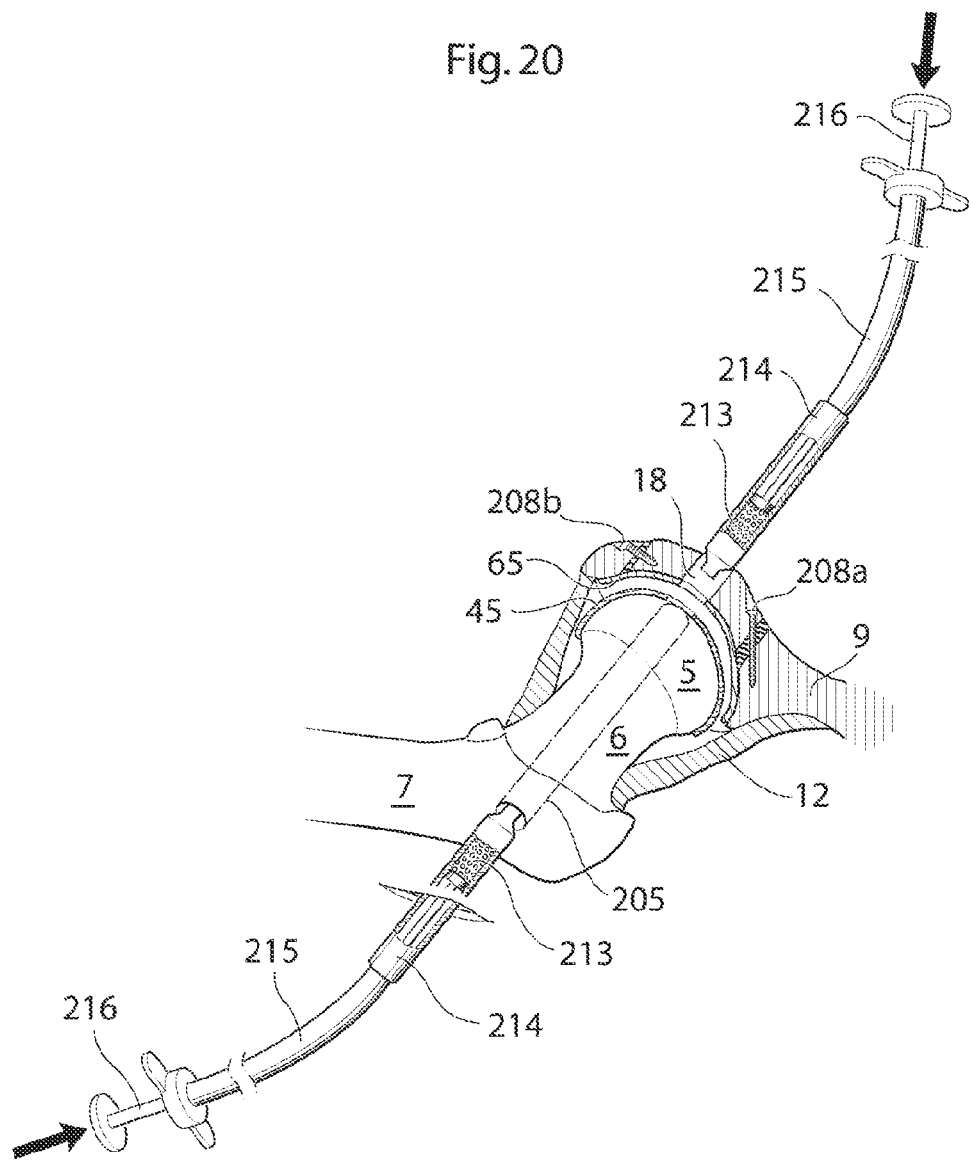

MEDICAL DEVICE AND METHOD FOR TREATMENT OF HIP JOINT

This application is a continuation of U.S. application Ser. No. 13/383,039, filed Jan. 9, 2012, which is the U.S. national phase of International Application No. PCT/SE10/50815, filed Jul. 12, 2010, which designated the U.S. and claims the benefit of U.S. Provisional Application Nos. 61/213,814, 61/229,739, 61/229,743, 61/229,745, 61/229,746, 61/229,747, 61/229,748, 61/229,751, 61/229,752, 61/229,755, 61/229,761, 61/229,767, 61/229,778, 61/229,786, 61/229,789, 61/229,796, 61/229,735 and 61/229,738, all filed on Jun. 7, 2009 and priority from Swedish patent application nos. 0900958-0, 0900978-8, 0900976-2, 0900974-7, 0900973-9, 0900972-1, 0900970-5, 0900969-7, 0900968-9, 0900966-3, 0900965-5, 0900963-0, 0900962-2, 0900960-6, 0900959-8, 0900957-2 and 0900981-2, all filed Jun. 7, 2009, the entire contents of each of which are hereby incorporated by reference in this application.

FIELD OF INVENTION

The present invention relates generally to a medical device for use in a surgical or laparoscopic/arthroscopic method of operating in an area of the hip joint and its surroundings.

BACKGROUND

Hip joint Osteoarthritis is a syndrome in which low-grade inflammation results in pain in the hip joints, caused by abnormal wearing of the Cartilage that acts as a cushion inside if the hip joint. This abnormal wearing of the cartilage also results in a decrease of the joints lubricating fluid called Synovial fluid. Hip joint Osteoarthritis is estimated to affect 80% of all people over 65 years of age, in more or less serious forms.

The present treatment for hip osteoarthritis comprises NSAID drugs, local injections of Hyaluronic acid or Glucocorticoid to help lubricating the hip joint, and replacing parts of the hip joint with a prosthesis through hip joint surgery.

The replacing of parts of the hip joint is one of the most common surgeries to date performed at hundreds of thousands of patients in the world every year. The most common method comprises placing a metal prosthesis in Femur and a plastic bowl in Acetabulum. This operation is done through an incision in the hip and upper thigh and through Fascia Lata and the lateral muscles of the thigh. To get access to the joint, the supporting Fibrous Capsule attached to Femur and Ilium needs to be penetrated, making it difficult to get a fully functional joint after the surgery. Femur is then cut at the neck with a bone saw and the prosthesis is placed in femur either with bone cement or without. Acetabulum is slightly enlarged using an Acetabular reamer, and the plastic bowl is positioned using screws or bone cement.

The surgery typically requires one week of hospitalization due to the increased risk of infection. The recovery process is on average about 6 weeks, but even after this period the patient should not perform any physical activates that places large strain on the joint.

It would therefore be desirable to have a medical device that could enable a less invasive surgical or laparoscopic/arthroscopic method. It would further be preferable to have a method of operating that could shorten the time for recovery of the patient, and reducing the amount of affected large blood vessels, thus reducing the risk of blood clots.

SUMMARY

A medical device for delivering an action to an area of a hip joint or its surroundings is provided. The hip joint comprising a collum femur and a ball shaped caput femur, being the proximal parts of the femoral bone, and an acetabulum, being a bowl shaped part of the pelvic bone. The medical device comprising an elongated member, having a length axis along its elongated distribution, and a first portion being adapted to enter the body of the patient, said first portion of said elongated member having a first portion cross-section area substantially perpendicular to the length axis of the elongated member. The first portion comprises a holding member adapted to hold said mechanical element inside the body of said patient, and a mounting portion. The first portion further comprises a mechanical element comprising at least one mounting recess for mounting the mechanical element onto the mounting portion in a direction substantially perpendicular to the elongated member, wherein said mechanical element is adapted to be used during an operation in the hip joint or its surroundings, when placed inside the body. The first portion is adapted to pass through a hole in a bone of the patient, the hole having a hole cross-section area. The first portion cross-section area is smaller than said hole cross-section area, and said mechanical element, having a functional status ready to deliver said action inside the body when held by said holding member inside the body of the patient, has a mechanical element cross-sectional area substantially perpendicular to the length axis of the elongated member, being substantially larger than said first portion cross-section area and unable to pass through the hole when said mechanical element is in said functional status.

According to one embodiment the mechanical element cross-sectional area is in the interval 1.2-2 times larger than said first portion cross-sectional area or in the interval 2-3 times larger than said first portion cross-sectional area.

According to another embodiment the first portion of the elongated member is long enough to pass through a hole in the femoral bone, through the hip joint and through a hole in the pelvic bone entering the abdominal cavity.

According to yet another embodiment, the elongated member is long enough to pass through a hole in the femoral bone, through the hip joint and through a hole in the pelvic bone, entering the abdominal cavity and through the pelvic bone on the opposite side and further out through the skin of the patient, or through the skin of the patient, through the pelvic bone, through the abdominal cavity, through the pelvic bone on the opposite side, and into the hip joint.

Alternatively, a medical device for delivering an action to an area of a hip joint and its surroundings of a human patient is provided. The hip joint comprises a collum femur and a caput femur, both being the proximal part of the femoral bone. Furthermore the hip joint comprises an acetabulum, being a bowl shaped part of the pelvic bone. The medical device comprises an elongated member, wherein said elongated member is adapted to transfer force from said operating device to said area of said hip joint, and its surroundings, through a hole in said collum femur.

Tool Fixating Member

According to one embodiment the medical device further comprises a tool fixating member in connection with said force transferring member. The tool fixating member could be adapted to transfer force from the elongated member to a tool.

According to one embodiment the tool comprises at least one drilling tool, which could be adapted to create a hole in the pelvic bone from the abdominal side of said pelvic bone.

According to another embodiment the tool comprises at least one reaming tool, which could be adapted to ream the acetabulum and/or the caput femur.

According to one embodiment the tool comprises at least one tool for fixating a fixation element to said area of said hip joint. The fixation element could comprise a fixation element selected from a group consisting of: at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members.

According to one embodiment the tool comprises at least one fluid injecting tool. The fluid injecting tool could be adapted to inject adhesive, bone cement and/or a lubricating fluid.

According to another embodiment the tool comprises at least one tool for manipulating an implantable device, which could be an artificial acetabulum surface and/or an artificial caput femur surface.

Elongated Member

The elongated member could be adapted for rotational, reciprocating or oscillating movement, and could comprise a rod or a wire, which in turn could comprise a part or section adapted to be bent.

According to one embodiment the elongated member is adapted to be supported in at least a first and a second supporting point. The first and said second supporting point could be separated from each other. In one embodiment the first supporting point is a supporting point in the femoral bone and the second supporting point is a supporting point in the pelvic bone.

According to one embodiment the medical device is adapted to control the placing of at least one prosthetic part in the hip joint.

Operating Device

According to one embodiment the medical device further comprises an operating device adapted to create force. The operating device could be connected to the force transferring member.

The operating device could comprise a motor, which could be an electrical motor, a hydraulic motor or a pneumatic motor.

According to one embodiment the operating device is an operating device adapted for manual manipulation.

According to yet another embodiment the operation device is adapted to connect to the elongated member in the abdomen of the body and/or outside the body lateral of the proximal femoral bone and/or outside the body, lateral on the opposite side of said hip joint of said body outside the pelvic bone.

According to one embodiment the elongated member is adapted to receive the force from an operation device in the abdomen. It is also conceivable that the elongated member is adapted to receive the force from an operation device outside the body, lateral of the proximal femoral bone and/or outside the body, lateral on the opposite side of the hip joint the body outside the pelvic bone.

Centering Device

According to one embodiment the medical device comprises an artificial acetabulum or an artificial acetabulum surface, wherein said elongated member is adapted to center and hold the artificial acetabulum or the artificial acetabulum surface during fixation in the hip joint.

According to another embodiment, the medical device comprises an artificial caput femur or an artificial caput femur surface. The elongated member is adapted to center and hold the artificial caput femur or artificial caput femur during fixation in the hip joint.

According to yet another embodiment the elongated member is adapted to center and hold both the artificial caput femur or the artificial caput femur surface and the artificial acetabulum or the artificial acetabulum surface during fixation in the hip joint.

The artificial caput femur surface, according to any of the embodiments herein could comprise a convex form towards the center of the hip joint, and the artificial acetabulum surface could comprise a concave form towards the center of the hip joint, and be constructed to be placed in the hip joint in a opposite position towards each other, thus; the artificial convex caput femur surface is adapted to be fixated to the pelvic bone of the human patient, and the artificial concave acetabulum surface is adapted to be fixated to the femoral bone of the human patient.

According to yet another embodiment the artificial acetabulum or artificial acetabulum surface is adapted to be centered and held by the elongated member, during fixation in the hip joint.

According to one embodiment the artificial caput femur or artificial caput femur surface is adapted to be centered and held by the elongated member, during fixation in the hip joint.

Method

Further, a method of delivering force to an area of a hip joint of a human patient is provided. The hip joint comprises a collum femur, being the proximal part of the femoral bone, a caput femur, being the upper extremity of the femoral bone, and an acetabulum, being a bowl shaped part of the pelvic bone. The method comprises the steps of: penetrating the skin of a lateral section of the thigh, creating a hole in the collum femur, along a length axis thereof, reaching an area of said hip joint, placing an elongated member in said hole. The elongated member reaches the area of the hip joint, and the elongated member is connected to an operating device delivering force to the area of the hip joint through the elongated member, by the connection with the operating device.

According to one embodiment, the method further comprises the step of fixating a tool to the elongated member.

According to one embodiment the first portion of the elongated member is adapted to be introduced into at least one of the femoral bone and the pelvic bone, and the elongated member is further adapted to be introduced into a hole in an artificial hip joint surface, when said artificial hip joint surface is placed inside the human body.

The elongated member according to could according to one embodiment be adapted to guide the artificial hip joint surface to a correct position inside the human body when the elongated member is introduced into said hole in the artificial hip joint surface.

The elongated member could further be adapted to be fixated to at least one of the femoral bone and the pelvic bone during, when said artificial hip joint surface is placed inside the human body.

The elongated member could further be adapted to be removed from at least one of the femoral bone and the pelvic bone when said artificial hip joint surface is placed inside the hip joint.

The elongated member could further be adapted to be removed from said artificial hip joint surface when said artificial hip joint surface is placed in said correct position inside the hip joint.

The elongated member could further be adapted to have a first and second state, wherein in said first state said elongated member is flexible, and wherein in said second state said elongated member is adapted to be less flexible than in said first state.

According to one embodiment the elongated member is adapted to guide an artificial hip joint surface in at least one axis, at least two axis, at least three axis or in at least one plane.

According to another embodiment the elongated member is adapted to be placed in a positioning hole of said artificial hip joint surface.

The artificial hip joint surface could comprise at least two artificial hip joint surface parts, and the elongated member could be adapted to be placed in a positioning hole in at least one of the at least two artificial hip joint surface parts.

The elongated member, having an area substantially perpendicular to its elongated distribution, could be adapted to be positioned in the positioning hole, being substantially circular.

The elongated member could according to other embodiments be adapted to be positioned in the positioning hole being substantially non-circular or having a cut circumference.

The elongated member could further be adapted to receive the artificial hip joint surface inserted into the hip joint through the hip joint capsule or through the pelvic bone.

According to yet another embodiment the elongated member is adapted to receive the artificial hip joint surface to be mounted onto the elongated member inside of the hip joint.

According to another embodiment the method further comprises the step of creating a hole in the pelvic bone using the tool.

According to one embodiment the method further comprises the step of reaming the acetabulum and/or the caput femur using the tool.

According to one embodiment the method further comprises the step of fixating the tool to the elongated member from the abdominal side of the pelvic bone.

According to one embodiment the method further comprises the step of fixating a fixation element to the area of the hip joint.

According to another embodiment the method further comprises the step of injecting a fluid into the area of the hip joint. The fluid could be an adhesive, bone cement and/or a lubricating fluid.

According to one embodiment the method further comprises the step of manipulating an implantable device in the area of the hip joint. The manipulation could comprise the step of fixating an artificial acetabulum surface to the pelvic bone and/or fixating an artificial caput femur surface to the femoral bone.

According to another embodiment the step of manipulating, comprises the step of; fixating an artificial acetabulum surface to the pelvic bone, and wherein the elongated member centers the artificial acetabulum surface, when the artificial acetabulum surface is fixated in the hip joint.

According to yet another embodiment, the step of manipulating comprises the step of; fixating an artificial caput femur surface to the femoral bone, wherein the elongated member centers the artificial caput femur surface, when the artificial caput femur surface is fixated in the hip joint.

A further method of centering an artificial hip joint surface in the hip joint of a human patient is provided, the hip joint comprising a collum femur, being the proximal part of the femoral bone, a caput femur, being the upper extremity of the femoral bone, and an acetabulum, being a bowl shaped part of the pelvic bone. The method comprises the steps of: penetrating the skin of a lateral section of the thigh, creating a hole in the collum femur, along a length axis thereof, reaching an area of the hip joint, placing an elongated member in the hole, the elongated member reaching centrally in the area of the hip joint. Furthermore the method comprises centering the artificial hip joint surface onto the elongated member, wherein the artificial hip joint surface comprises a center hole for guiding the force transferring member, and placing the artificial hip joint surface in a functional position in the hip joint.

The artificial hip joint surface above may comprise, an artificial convex caput femur or an artificial convex caput femur surface and/or an artificial concave acetabulum or an artificial concave acetabulum surface.

The step of delivering an action to the area of the hip joint could comprise the step of manipulating an implantable device in the area of the hip joint. The step of manipulating an implantable device could further comprise the step of fixating an artificial acetabulum surface to the pelvic bone.

The step of manipulating an implantable device could comprise the step of fixating an artificial caput femur surface to the femoral bone and/or the step of centering an artificial acetabulum surface using the elongated member and/or the step of fixating the artificial acetabulum surface to the pelvic bone.

According to another embodiment, the step of manipulating an implantable device could comprise the step of centering an artificial caput femur surface using the elongated member, and the step of fixating the artificial caput femur surface to the pelvic bone.

According to another embodiment the medical device could comprise an artificial acetabulum or an artificial acetabulum surface adapted to be centered and held by the elongated member during fixation in the hip joint. The method comprises the step of centering the artificial acetabulum or the artificial acetabulum surface using the elongated member.

According to one embodiment the medical device comprises an artificial caput femur or an artificial caput femur surface adapted to be centered and held by the elongated member, during fixation in said hip joint. The method, according to any of the embodiments above comprises the step of centering the artificial caput femur or the artificial caput femur surface using the elongated member.

According to another embodiment the step of penetrating the skin is performed at a lateral portion of the thigh.

According to one embodiment the step of creating a hole in bone comprises creating a hole along the length axis of the collum femur.

The method step of placing an artificial hip joint surface could comprises the step of placing an artificial convex caput femur or an artificial convex caput femur surface onto the pelvic bone or the step of placing an artificial concave acetabulum or an artificial concave acetabulum surface onto the femoral bone.

A method of centering an artificial hip joint surface in a hip joint of a human patient is further provided. The hip joint comprises a collum femur, being the proximal part of the femoral bone, a caput femur, being the upper extremity of the femoral bone, and an acetabulum, being a bowl shaped part of the pelvic bone. The method comprises the steps of: performing an abdominal operation, creating a hole in the pelvic bone from the abdominal side opposite the acetabulum, reaching an area of the hip joint, placing an elongated member in said hole passing into said femoral bone, dissecting the hip joint preparing for an artificial hip joint surface, placing an artificial hip joint surface in said hip joint, wherein said artificial hip joint surface having a guiding hole adapted to receive said elongated member, introducing said elongated member in said hole of said artificial hip joint surface, guiding said artificial hip joint surface using said elongated member, fixating said artificial hip joint surface in a functional position in said hip joint.

According to one embodiment the method step of placing an artificial hip joint surface comprises the step of placing an artificial convex caput femur or an artificial convex caput femur surface and/or the step of placing an artificial concave acetabulum or an artificial concave acetabulum surface.

The step of placing an artificial hip joint surface could comprise the step of placing an artificial concave acetabulum or an artificial concave acetabulum surface, and the step of placing an artificial convex caput femur or an artificial convex caput femur surface.

According to another embodiment the step of placing an artificial hip joint surface comprises the step of placing an artificial convex caput femur or an artificial convex caput femur surface onto the pelvic bone and/or the step of placing an artificial hip joint surface comprises the step of placing an artificial concave acetabulum or an artificial concave acetabulum surface onto the femoral bone.

Please note that any method or part of method may be combined with any other method or part of method to create any combination of methods or parts of methods.

BRIEF DESCRIPTION OF THE DRAWINGS

Embodiments will now be described, by way of example, with reference to the accompanying drawings, in which:

FIG. 5b shows the hip joint in section and different tools, FIG. 6 shows the hip joint in section when a tool for creating a hole in the pelvic bone is used, FIG. 7 shows the hip joint in section when a hole has been created in the pelvic bone, FIG. 11d-g shows the hip joint in section when a mechanical element is provided, FIG. 14 shows the hip joint in section when a prosthetic part has been placed in the hole in the pelvic bone, FIG. 20 shows the hip joint in section when a liquid is being injected in holes in the femoral bone and the pelvic bone.

DETAILED DESCRIPTION

An action in the hip joint is to be understood as a force, movement or insertion of any tool, prosthesis, prosthetic parts or fluid in the hip joint.

Force is to be understood as any kind of movement or torque that could be needed to perform a step in the medical treatment of a hip joint of a human patient. The force could be a rotating, reciprocating or oscillating movement, created by an operating device or manual manipulation. It is further conceivable that said force comprises two or more components which could be two or more rotating, reciprocating or oscillating components, or any combination thereof. The operating device could for example be an electrical, hydraulic or pneumatic motor.

Elongated member is to be understood as any element able to transfer an action or force according to the definition herein. The elongated member could be a stiff or flexible rod, shaft or wire. It is furthermore conceivable that the elongated member could have a part or section adapted to be bent such as a universal joint or at least two gear wheels or worm gears.

The mechanical element adapted to be fixated to the elongated member is to be understood as a tool or means for fixating a tool or a prosthetic part. A prosthetic part could be an artificial caput femur surface and/or an artificial acetabulum surface.

Figure 1:
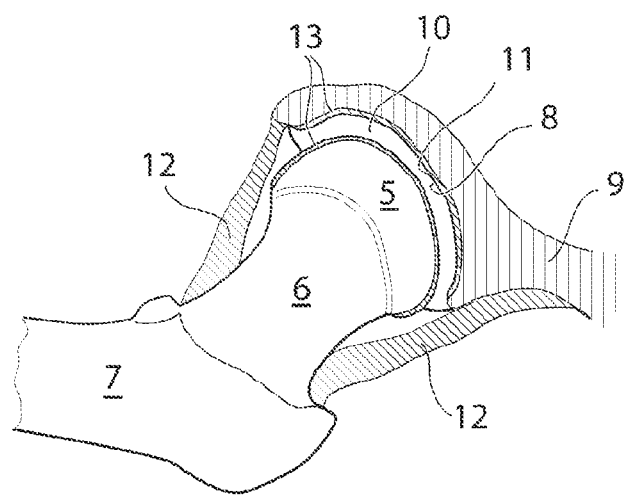
FIG. 1 shows the hip joint in section.

Area of the hip joint or its surroundings is to be understood as the immediate area of the hip joint as shown in FIG. 1, together with the abdominal, pelvic and inguinal areas which could be affected in an operation of the hip joint.

Fixation element is to be understood as a mechanical element which has properties for fixating or assisting in the fixation of prosthesis or a prosthetic part to a human patient.

Manipulating an implantable device is to be understood as the process of positioning a prosthesis or prosthetic part to a desired position in the human patient. For example the process of manipulating can comprise: rotating, turning, bending or attaching.

In the following a detailed description of embodiments will be given. In the drawing figures, like reference numerals designate identical or corresponding elements throughout the several figures. It will be appreciated that these figures are for illustration only and are not in any way restricting the scope of the invention. Thus, any references to direction, such as "up" or "down", are only referring to the directions shown in the figures. Also, any dimensions etc. shown in the figures are for illustration purposes.

FIG. 1 shows the hip joint of a human patient in section. The hip joint comprises a caput femur 5 placed at the very top of collum femur 6 which is the top part of the femoral bone 7. The caput femur is in connection with the acetabulum 8, which is a bowl shaped part of the pelvic bone 9. Both the caput femur surface 10 and the acetabulum surface 11 is covered with articular cartilage 13 which acts as a cushion in the hip joint. In patients with hip joint osteoarthritis, this articular cartilage 13 is abnormally worn down due to a low grade inflammation. The hip joint is surrounded by the hip joint capsule 12 which provides support for the joint and hinders luxation. After conventional hip joint surgery, penetrating the hip joint capsule 12, the capsule 12 is dramatically weakened due to the limited healing possibilities of its ligament tissue. By performing hip joint surgery without damaging the hip joint capsule 12 the patient can fully recover and place equal amount of strain on an artificial joint as is possible on a natural one.

Figure 2:
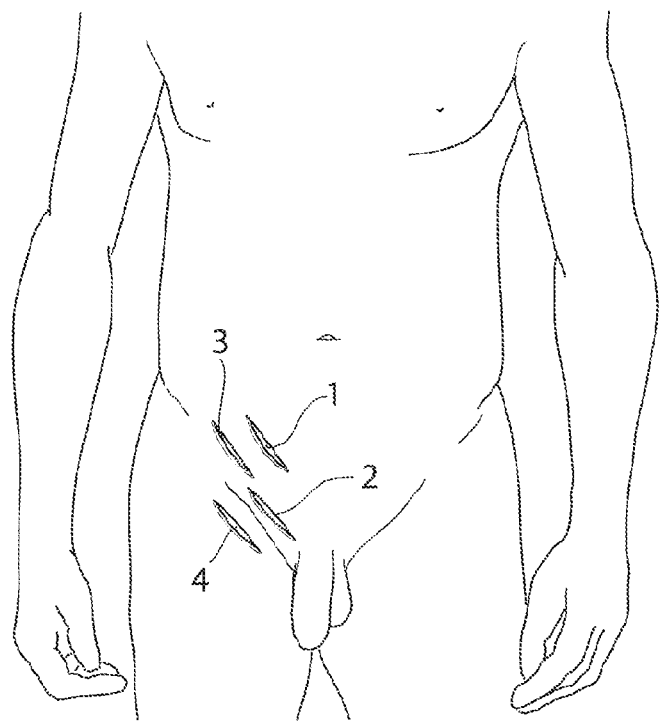
FIG. 2 shows a frontal view of a human patient when incisions have been performed in a surgical method.

FIG. 2 shows a frontal view of a human patient when an incision for reaching an area of the hip joint through the pelvic bone in a surgical method has been performed. According to one embodiment the incision 1 is made in the abdominal wall of the human patient. The incision 1 passes preferable through the rectus abdominis and through the peritoneum, in to the abdomen of the human patent. In a second embodiment the incision 2 is conducted through the rectus abdominis and in to the pelvic area, below peritoneum. According to a third embodiment the incision 3 is performed just between Illium and the surrounding tissue, an incision 3 which could enable the pelvic bone to be dissected with very little penetration of fascia and muscular tissue. According to a fourth embodiment the incision 4 is made in the inguinal channel. In all of the four embodiments the tissue surrounding the pelvic bone 9 in the area opposite to acetabulum is removed or penetrated which enables the surgeon to reach the pelvic bone 9.

Figure 3:
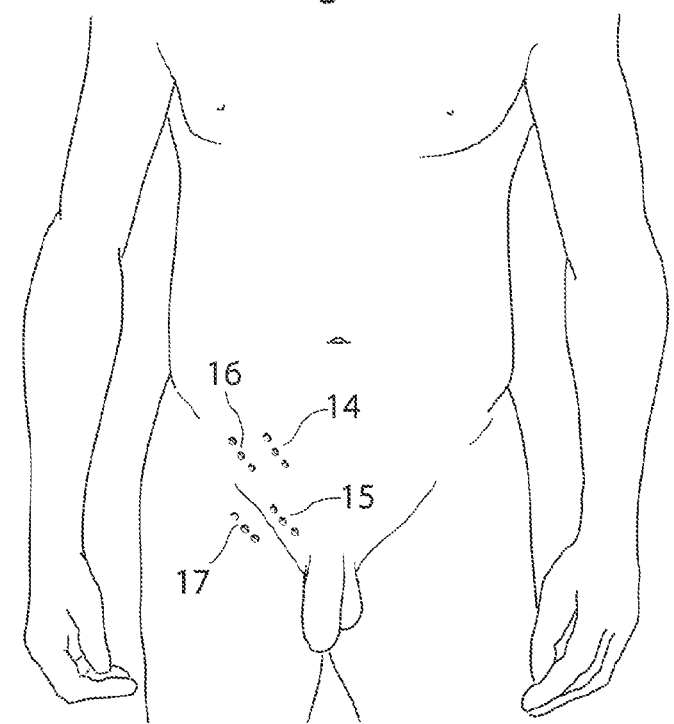
FIG. 3 shows a frontal view of a human patient when incisions have been performed in a laparoscopic/arthroscopic method.

FIG. 3 shows a frontal view of a human patient when small incisions for reaching an area of the hip joint through the pelvic bone in a laparoscopic/arthroscopic method has been performed. According to a first embodiment the incisions 14 is made in the abdominal wall of the human patient. The small incisions enable the surgeon to insert laparoscopic trocars into the abdomen of the human patient. According to the first embodiment the incisions 14 passes through the rectus abdominis and peritoneum, in to the abdomen of the human patent. According to a second embodiment the small incisions 15 is conducted through the rectus abdominis and in to the pelvic area, below peritoneum. According to a third embodiment the small incisions 16 is performed just between Illium and the surrounding tissue, an incision 16 which could enable the pelvic bone to be dissected with very little penetration of fascia and muscular tissue. According to a fourth embodiment the incision 17 is made in the inguinal channel. In all of the four embodiments the tissue surrounding the pelvic bone 9 in the area opposite to acetabulum 8 is removed or penetrated which enables the surgeon to reach the pelvic bone 9.

Figure 4:
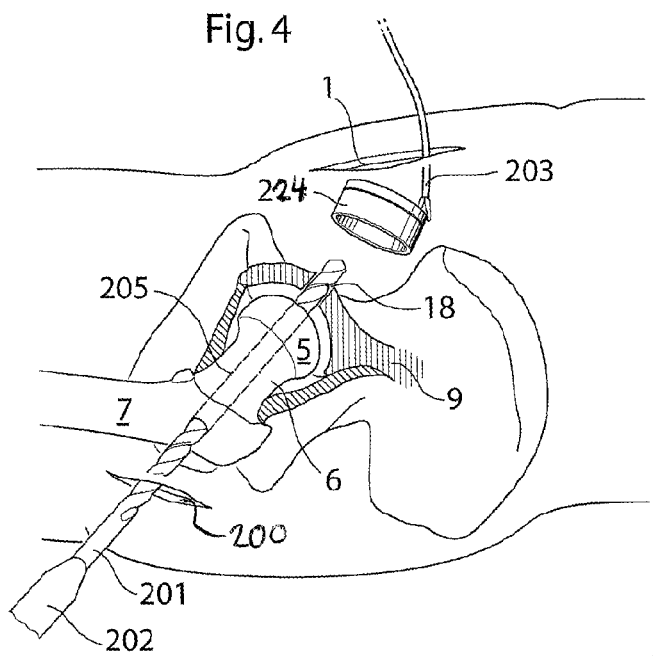
FIG. 4 shows the human patient in section when a tool is provided from the abdominal side of the pelvic bone.

FIG. 4 shows a human patient in section when an incision 1 is made in the abdominal wall of the human patient, and a second incision 200 in made in the lateral part of the left thigh. A drilling member 201 has been introduced through the incision 200 in the thigh, penetrating the fascia lata, and reaching the femoral bone 7. After the drilling member 201 has made contact with the femoral bone 7, a drilling process is started which creates a hole 205 in the cortical bone of the femoral bone 7 and into the cancellous bone of the femoral bone 7, the hole 205 then propagates along a length axis of the collum femur 6 and eventually reaches the caput femur 5, from the inside thereof. The caput femur 5 is penetrated from the inside and the drilling member 201 continues to the acetabulum 8 which is a bowled shaped part of the pelvic bone 9. The drilling member 201 penetrates the pelvic bone 9 and continues into the abdominal area of the human patient. The drilling member 201 is then retracted from the hole 205 which leaves a hole 205 reaching from the lateral side of the thigh, to the area of the hip joint. The drilling member 201 is powered by an operating device 202 which could be an electrically, hydraulically or pneumatically powered operating device 202.

After the hole 205 has been created along a length axis of the collum femur 6, an elongated member 206 is inserted through the hole 205. The elongated member 206 could be a tubular or solid shaft, or a flexible member 206b such as a wire.

Figure 5A:
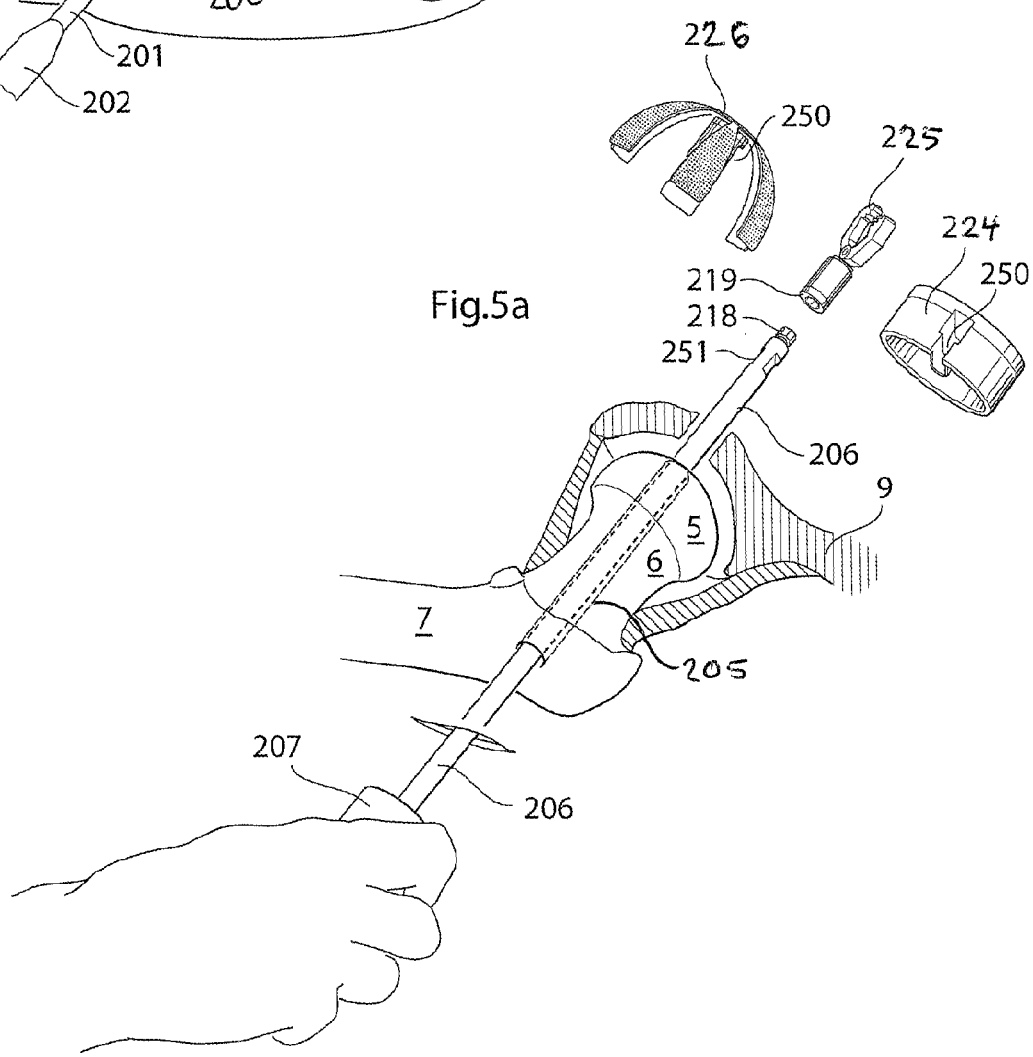
FIG. 5a shows the hip joint in section and different tools.

FIG. 5a shows the hip joint in section when an elongated member 206 has been inserted through the hole 205 in the femoral bone 7. The elongated member 206 comprises a tool fixating member/holding member 218 positioned on the end of the elongated member 206. The tool fixating member/holding member 218 could comprise a screw-thread or a bayonet joint which could be activated to fixate a mechanical element 224, such as a tool 224,225,226, to the elongated member 206, by means of manual manipulation or an operating device 202.

The mechanical element is adapted for delivering an action to an area of a hip joint or its surroundings. The elongated member 206 further comprises a mounting portion 251 to which a mechanical element 224 can be mounted. The mechanical element 224 comprises a mounting recess 250 for mounting the mechanical element 224 onto the mounting portion 251 in a direction substantially perpendicular to the elongated member 206.

The mechanical element 224 could be a tool 224 for creating a hole in the pelvic bone 9, a tool 225 for manipulating an implantable device such as a prosthesis or a prosthetic part, or a tool 226 for reaming the acetabulum 8 and/or the caput femur 5. The tools comprise a fixating member 219 which acts together with the tool fixating member/holding member 218 on the elongated member 206 to fixate the tool 224,225,226 to the elongated member 206. The tools 224,225,226 are inserted through the incision in the abdominal region, as shown in FIG. 4. where a tool 224 for creating a hole in the pelvic bone 9 is inserted through an incision 1 in the abdominal region of the human patient using a tool introducing member 203. The elongated member 206 has a length axis along its elongated distribution having a first portion cross-section area substantially perpendicular to the length axis of the elongated member, the elongated member 206 comprises a holding member 218 adapted to hold said mechanical element inside the body of said patient, and a mounting portion 251. The mechanical element 224,225,226 comprises at least one mounting recess 250 for mounting the mechanical element 224,225,226 onto the mounting portion 251 in a direction substantially perpendicular to the elongated member 206. The mechanical element 224,225,226 is adapted to be used during an operation in the hip joint or its surroundings, when placed inside the body. The elongated member 206 is adapted to pass through a hole in a bone of the patient, the hole having a hole cross-section area. The first portion cross-section area is smaller than the hole cross-section area, and the mechanical element has a functional status, ready to deliver an action inside the body. The mechanical element 224,225,226 cross-sectional area substantially perpendicular to the length axis of the elongated member 206, being substantially larger than the first portion cross-section area and unable to pass through the hole when said mechanical element is in said functional status.

The elongated member 206 is according to this embodiment long enough to pass through a hole in the femoral bone 7, through the hip joint and through a hole in the pelvic bone 9 entering the abdominal cavity.

FIG. 5*b* shows the hip joint in section when a elongated member 206*b* has been inserted through the hole 205. According to this embodiment the elongated member 206*b* is a flexible elongated member 206*b*, such as a wire, enabling the elongated member 206*b* to be bent for simplified handling and/or improved reach. The elongated member 206*b* comprises a tool fixating member 218 positioned on the end of the elongated member 206*b*. The tool fixating member 218 could be activated to fixate a tool 224,225,226 to the elongated member 206*b*, by means of manual manipulation or an operating device 202. The elongated member 206 further comprises a mounting portion 251 to which a mechanical element 224 can be mounted. The mechanical element 224 comprises a mounting recess 250 for mounting the mechanical element 224 onto the mounting portion 251 in a direction substantially perpendicular to the elongated member 206. FIG. 5 further shows a tool for creating a hole 224 in the pelvic bone 9, a tool 225 for manipulating an implantable device such as a prosthesis or a prosthetic part, and a tool 226 for reaming the acetabulum 8 and/or the caput femur 5. The tools comprises a fixating member 219 which acts together with the tool fixating member 218 on the elongated member 206*b* to fixate the tool 224,225,226 to the elongated member 206. The tools 224,225,226 are inserted through the incision in the abdominal region, as shown in FIG. 4, where a tool 224 for creating a hole in the pelvic bone 9 is inserted through an incision 1 in the abdominal region of the human patient using a tool introducing member 203. The elongated member 206 has a length axis along its elongated distribution having a first portion cross-section area substantially perpendicular to the length axis of the elongated member, the elongated member 206 comprises a holding member 218 adapted to hold said mechanical element inside the body of said patient, and a mounting portion 251. The mechanical element 224,225,226 comprises at least one mounting recess 250 for mounting the mechanical element 224,225,226 onto the mounting portion 251 in a direction substantially perpendicular to the elongated member 206. The mechanical element 224,225,226 is adapted to be used during an operation in the hip joint or its surroundings, when placed inside the body. The elongated member 206 is adapted to pass through a hole in a bone of the patient, the hole having a hole cross-section area. The first portion cross-section area is smaller than the hole cross-section area, and the mechanical element has a functional status, ready to deliver an action inside the body. The mechanical element 224,225,226 cross-sectional area substantially perpendicular to the length axis of the elongated member 206, being substantially larger than the first portion cross-section area and unable to pass through the hole when said mechanical element is in said functional status.

The elongated member 206 is according to this embodiment long enough to pass through a hole in the femoral bone 7, through the hip joint and through a hole in the pelvic bone 9 entering the abdominal cavity.

FIG. 6 shows the hip joint in section when a tool 224 for creating a hole 18 in the pelvic bone is fixated to the tool fixating member 219 on the elongated member 206. When the tool 224 for creating a hole in the pelvic bone 9 is applied to the elongated member 206, the elongated member 206 is preferably operated using an operating device 202, which could be an electrical, hydraulic or pneumatic operating device. The tool for creating a hole in the pelvic bone 9 comprises a bone contacting organ 22 which is adapted to create the hole 18 in the pelvic bone 9 through a sawing, drilling or milling process powered by a rotating, vibrating or oscillating movement of the elongated member 206.

FIG. 7 shows the hip joint in section when the hole 18*b* in the pelvic bone 9 has been created. According to the embodiment shown the hole 18*b* is created through the creation of a bone plug 207 which can be adapted to be replaced after the steps of the operation performed through the hole 18*b* in the pelvic bone 9 has been concluded.

Figure 8:
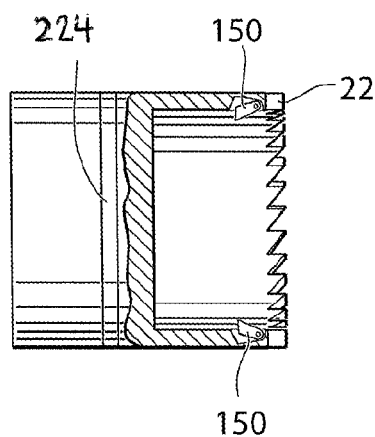
FIG. 8 shows a tool adapted to create a hole in the pelvic bone in further detail.

FIG. 8 shows the tool 224 for creating a hole 18*b* in the pelvic bone 9 in further detail. The bone contacting organ 22 is according to this embodiment adapted to create a bone plug 207. The tool 204 further comprises two holding members 150 for holding said bone plug 207 in place after it has been removed from the pelvic bone 9 of the human patient.

Figure 9:
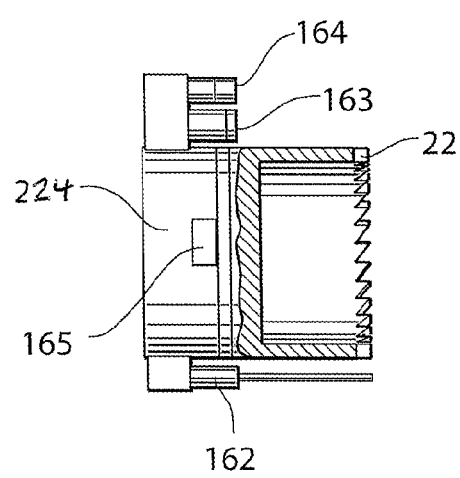
FIG. 9 shows a tool adapted to create a hole in the pelvic bone in further detail.

FIG. 9 shows the tool 224 for creating a hole 18*b* in the pelvic bone 9 according to an embodiment wherein said tool further comprises at least one of: at least one camera 163, at least one light source 164, at least one measurement device 162 for measuring the depth of said hole 18*b* in the pelvic bone 9 and at least one torque meter 165 for sensing the torque exerted on the bone contacting organ 22 from the connection with the elongated member and the operating device 202.

After the step of creating a hole in the pelvic bone has been concluded the surfaces of the acetabulum 8 and/or the caput femur 5 needs to be prepared.

Figure 10:
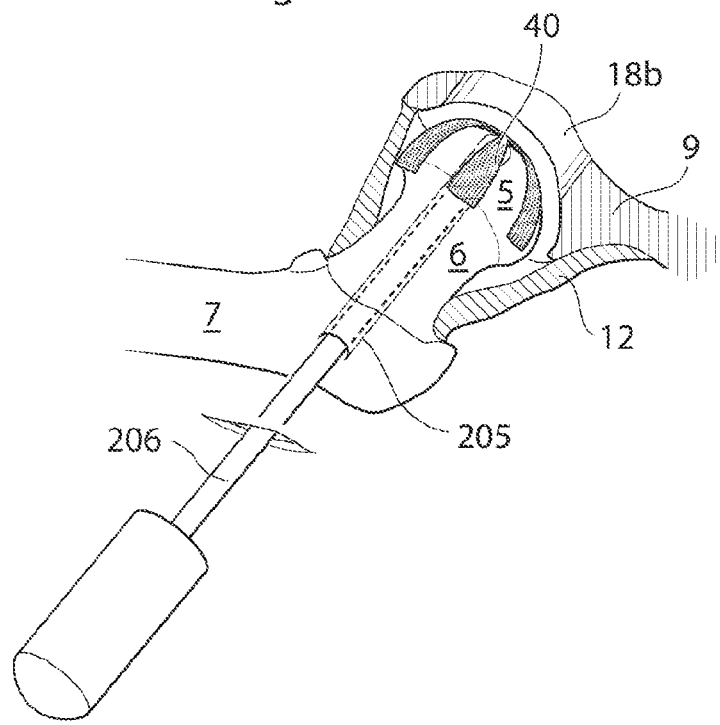
FIG. 10 shows the hip joint in section when a tool adapted to ream is used.

FIG. 10 shows the reaming of the acetabulum 8 and/or the caput femur 5 using a reamer 226 comprising reaming blades 40. The reamer 226 is adapted to be introduced through the pelvic bone 9 through an incision as shown in FIG. 2. The reamer 226 is operated through manual manipulation or an operating device 202.

Figure 11A:
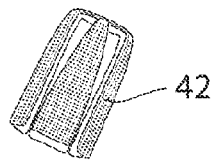
FIG. 11a-c shows an expandable reamer in further detail.

FIG. 11*a* shows the reamer 226 according to an embodiment where the reamer 226 is adapted to be expandable. The reaming blades 42 are folded which facilitates the introduction of the reamer 226 through the hole 18*b* in the pelvic bone 9.

Figure 11B:
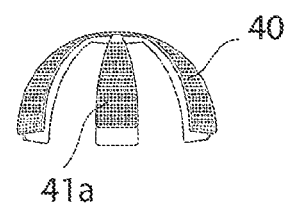

FIG. 11*b* shows the expandable reamer in its reaming state with the reaming blades 40 unfolded. The reaming blades 40 comprise an abrasive material which removes material, shapes and smoothens the surface of the acetabulum 8 and/or the caput femur 5. 41*a* denotes the abrasive material on the outside of the reaming blade 40, adapted to ream the acetabulum 8 surface.

Figure 11C:
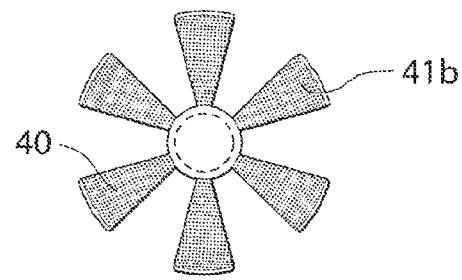

FIG. 11*c* shows the expandable reamer from the inside thereof, with the reaming blades 40 and the abrasive material 41*b* adapted to ream the caput femur 5.

After the surfaces of the caput femur 5 and/or the acetabulum 8 has been prepared the step of providing the surfaces with an artificial acetabulum surface 65 and/or caput femur surface 65 is performed.

FIG. 11*d* shows the medical device for delivering an action to an area of a hip joint or its surroundings, inside a human body. The hip joint of a patient comprises a collum femur 6 and a ball shaped caput femur 5, being the proximal parts of the femoral bone 7, and an acetabulum 8, being a bowl shaped part of the pelvic bone 9. The medical device according to the embodiment shown comprises an elongated member 206, having a length axis along its elongated distribution, comprising a first portion 206', adapted to enter the body of the patient, and a mechanical element 226, such as a reaming tool 226, adapted to be used during an operation in the hip joint or its surroundings, inside the body. The first portion 206' of the elongated member comprises a holding member 218, such as a tool fixating member 218, adapted to hold the mechanical element 226 inside the body of the patient, wherein the first portion of the elongated member 206' have a first portion cross-section area 247, shown in the section A-A, substantially perpendicular to the length axis of the elongated member 206. The first portion 206' is adapted to pass through a hole 205, in a bone of the patient, the hole 205 having a hole cross-section area 248, shown in section A-A. The first portion cross-section area 248, is adapted to be smaller than said hole cross-section area 247. The mechanical element 226 is in FIG. 11d shown in its functional status, ready to deliver an action inside the body, when held by the holding member 246 inside the body of the patient. The mechanical element 226 is adapted to have a mechanical element cross-sectional area 249, shown in section B-B, substantially perpendicular to the length axis of the elongated member 206, substantially larger than the first portion 206' cross-sectional area 247 and adapted to be unable to pass through the hole 205, when the mechanical element 226 is in the functional status. FIG. 11d furthermore shows the second portion 206" of the elongated member 206 adapted to remain outside of the body of the patient when the medical device is in use. The second portion 206" of the elongated member 206 could be adapted to be connected to an operating device 202 for operating the medical device. The mechanical element shown in FIG. 11d is a reaming tool, however the mechanical element could be any mechanical element for delivering any action, such as drilling, reaming, placing, connecting attaching, fixating, delivering an object, delivering a fluid or providing an optical view of the hip joint.

FIG. 11e shows the medical device according to an embodiment in which the first portion of the elongated member 240 is adapted to pass through the skin of the patient, through the pelvic bone 9", through the abdominal cavity, through the pelvic bone 9' on the opposite side, and into the hip joint.

FIG. 11f shows the elongated member 240 further detail, first in a state in which a protective sleeve is advanced for covering the drilling member 201 and thereby protecting the organs and tissue of the human body from the drilling member. Below, the drilling member is shown in a second state, in which the protective sleeve is refracted and thereby exposing the drilling member 201 and enabling the drilling member 201 to create a hole in bone.

Figure 11G:
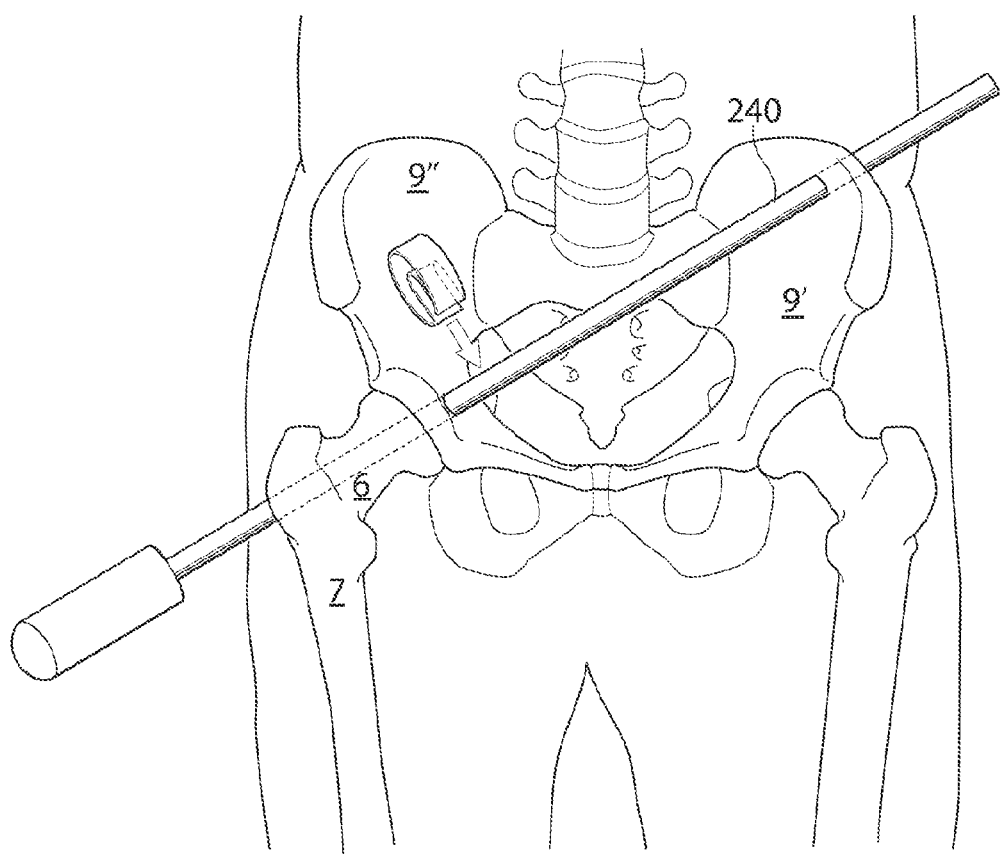

FIG. 11g shows the medical device according to an embodiment in which the first portion of the elongated member 240 is adapted to enter the body of the patient is long enough to pass through a hole in the femoral bone 7, through the hip joint and through a hole in the pelvic bone 9' entering the abdominal cavity and through the pelvic bone 9" on the opposite side and further out through the skin of the patient. The arrow shows the mounting direction of a mechanical element comprising at least one mounting recess for mounting the mechanical element onto the mounting portion of the elongated member in a direction substantially perpendicular to the elongated member.

Figure 12:
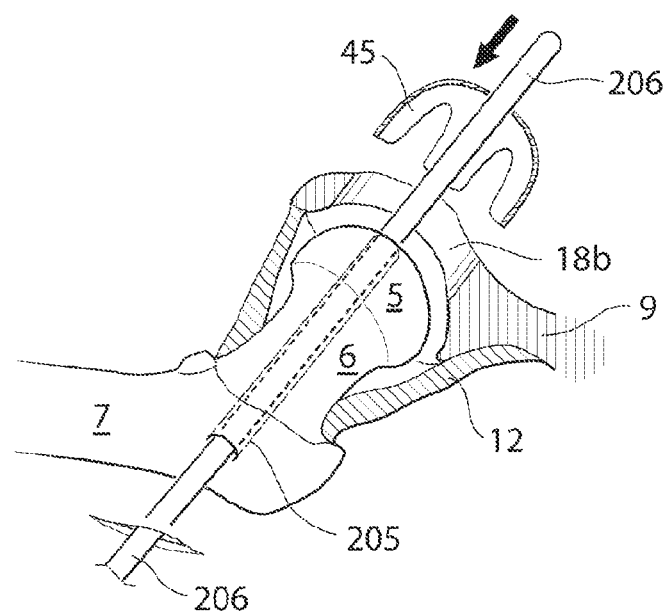
FIG. 12 shows the hip joint in section when an artificial hip joint surface is provided, FIG. 13a,b shows a prosthetic part for insertion in a hole in the pelvic bone.

FIG. 12 shows the step of providing an artificial caput femur surface 45 which is inserted through the incision according to FIG. 2 or FIG. 3. The artificial caput femur surface 45 is then mounted on to the elongated member 206 which acts a guide for the surface 45, facilitating the introduction and fixation of said surface 45. However it is furthermore conceivable that the elongated member is replaced by a guiding rod (not shown) adapted to guide the artificial caput femur surface 45 on to the caput femur 5.

FIG. 13a shows, schematically how a prosthetic part 98 is inserted in a hole 18b in the pelvic bone 9. The prosthetic part 98 comprises supporting members 99, which are adapted to support the weight of the human patient through the connection with the pelvic bone 9. The prosthetic part 98 is guided by the elongated member 900 through a guiding hole 910 being placed centrally in the prosthetic part 98. The supporting members 99 corresponds to sections in the hole 18b in the pelvic bone 9, which enables the insertion of the prosthetic part 98 through the hole 18b in the pelvic bone 9, and enables the prosthetic part 98 to carry the load from the human patient through the connection with the pelvic bone 9. The artificial acetabulum surface 65 could be a part of the prosthetic part 98 or a part adapted to be placed in the hip joint before the prosthetic part 98.

FIG. 13b shows the prosthetic part 98 when inserted and rotated to carry the load placed on the acetabulum surface 65 through the connection with the pelvic bone 9.

FIG. 14 shows the hip joint in section when a prosthetic part 98 has been provided. The supporting members 99 are placed in connection with the pelvic bone 9. The artificial acetabulum surface 65 is herein integrated with the prosthetic part 98.

Figure 15:
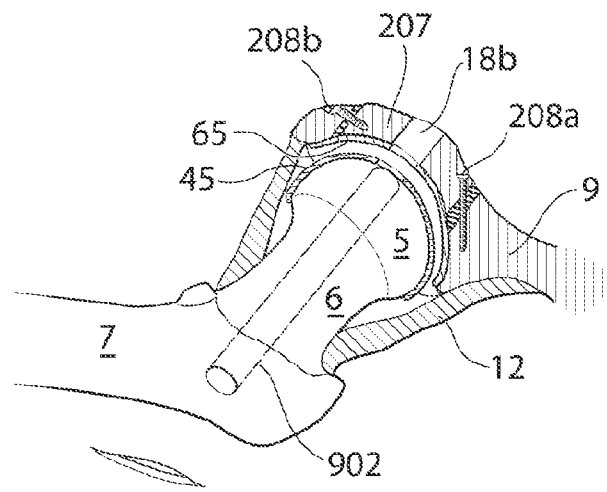
FIG. 15 shows the hip joint in section when a bone plug have been placed in the hole in the pelvic bone.

FIG. 15 shows the hip joint in section when the bone plug 207 has been replaced after an artificial caput femur surface 45 and an artificial acetabulum surface 65 has been provided. The bone plug 207 is fixated to the pelvic bone by means of screws 208a, 208b which can be placed from the pelvic bone 9 and into the bone plug 207, denoted 208b, and from the bone plug 207 and into the pelvic bone 9, denoted 208a. The elongated member 900 has been removed from the hole 902 in the femoral bone 7 and the pelvic bone 9.

Figure 16:
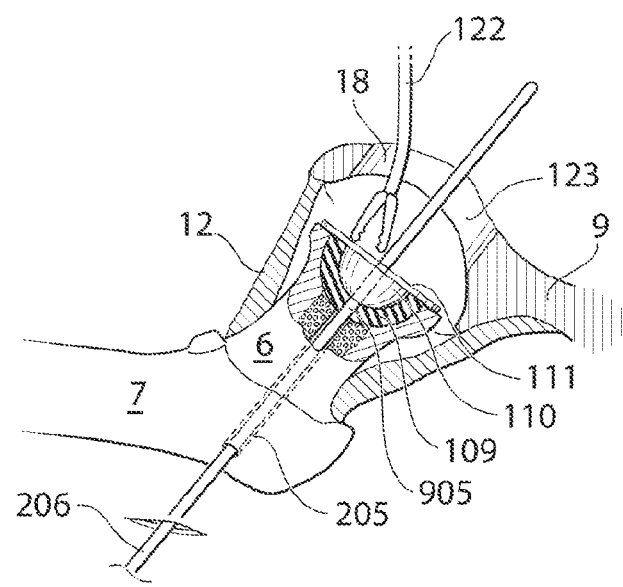
FIG. 16 shows the placing of an artificial acetabulum concave surface in the collum femur.

FIG. 16 shows the placing of a concave acetabulum surface 110 in the collum femur 6 from the abdominal side of the pelvic bone 9. The concave acetabulum surface 110 is guided by the elongated member 206 placed in a hole 205 in the femoral bone 7.

Figure 17:
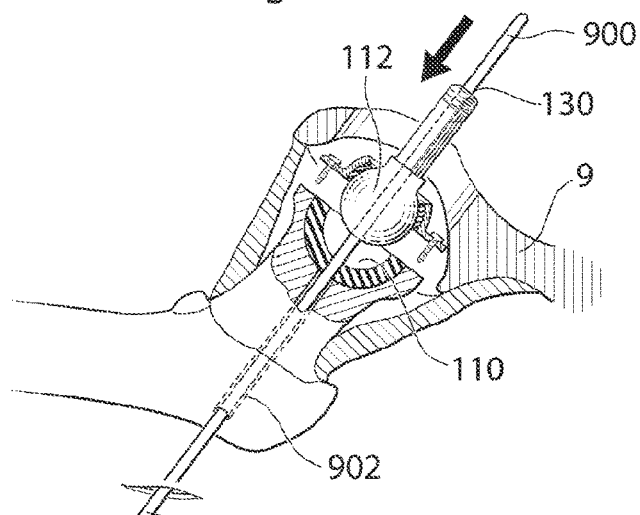
FIG. 17 shows the hip joint in section when a convex surface is placed in the concave surface in the collum femur.

FIG. 17 shows a convex caput femur surface being placed in the concave acetabulum surface 110 in the collum femur 6 from the abdominal side of the pelvic bone 9. The convex caput femur surface 112 is guided by the elongated member 900 and placed in the concave acetabulum surface 110, thus creating an opposite embodiment.

Figure 18:
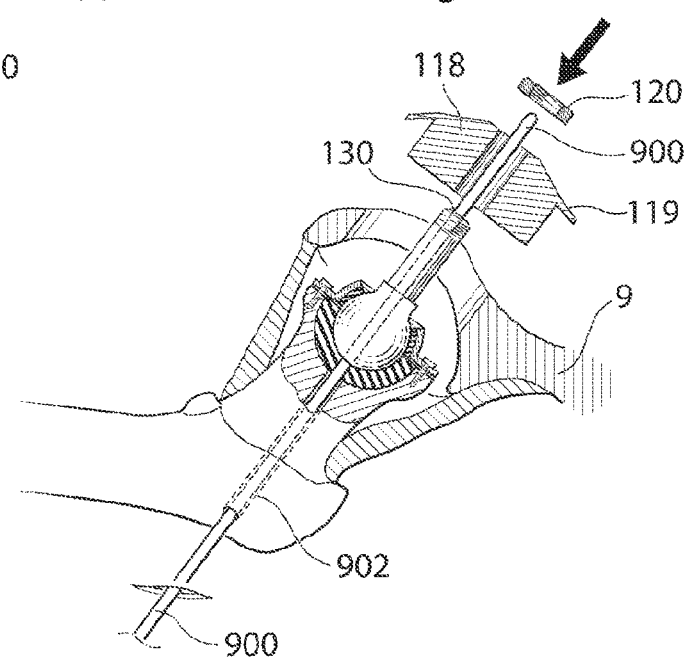
FIG. 18 shows the placing of a prosthetic part in a hole in the pelvic bone.

FIG. 18 shows the placing of a prosthetic part 118 in the pelvic bone 9 from the abdominal side of acetabulum 9. The prosthetic part comprising a hole in which the convex caput femur surface is placed and fixated by means of the screw threads 130 on the convex caput femur surface and the nut placed from the abdominal side of the pelvic bone 9.

Figure 19:
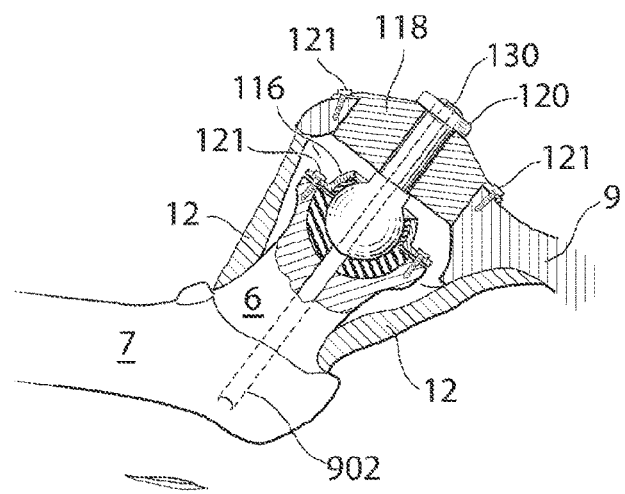
FIG. 19 shows the hip joint in section when the operating of FIGS. 16, 17 and 18 has been concluded.

FIG. 19 shows the hip joint in section after the operation shown in FIGS. 16, 17 and 18 has been concluded. The prosthetic part 118 has been fixated to the pelvic bone 9 using screws 121 placed in the pelvic bone 9 from the abdominal side of the pelvic bone 9, and the elongated member placed in the hole 902 in the femoral bone has been removed. The instant operation creates a hip joint in an opposite embodiment.

FIG. 20 shows the step of filling the holes 205, 18 created by the drilling member 201. The injecting members 214 is adapted to inject a fluid 213 into said hole 205, said fluid could be bone cement or another biocompatible fluid adapted to harden. The injecting members 214 comprises a piston 216 which transfers force through an injecting member 215 which could be flexible for facilitating the surgeon reaching the area where the hole 205 is located. The injecting members 215 comprises a piston 216 adapted to press the fluid 213 to be injected.

After the step of injecting a fluid 213 adapted to harden into the hole 205 is concluded the instruments used in the surgical or laparoscopic/arthroscopic method is retracted and the tissue is closed in layers.

Figure 21A:
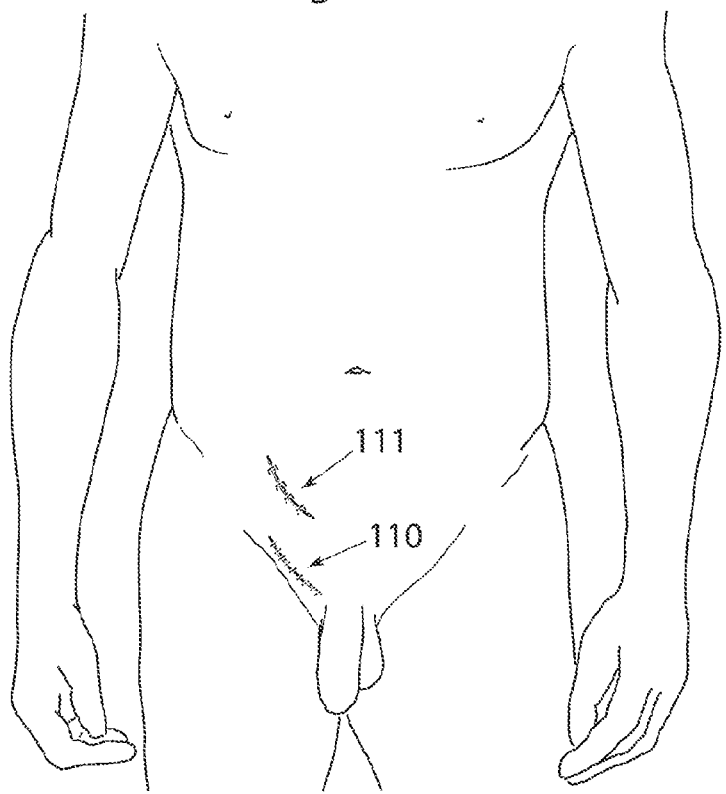
FIGS. 21a and 21b shows the suturing and stapling of the incisions made in the operation.
Figure 21B:
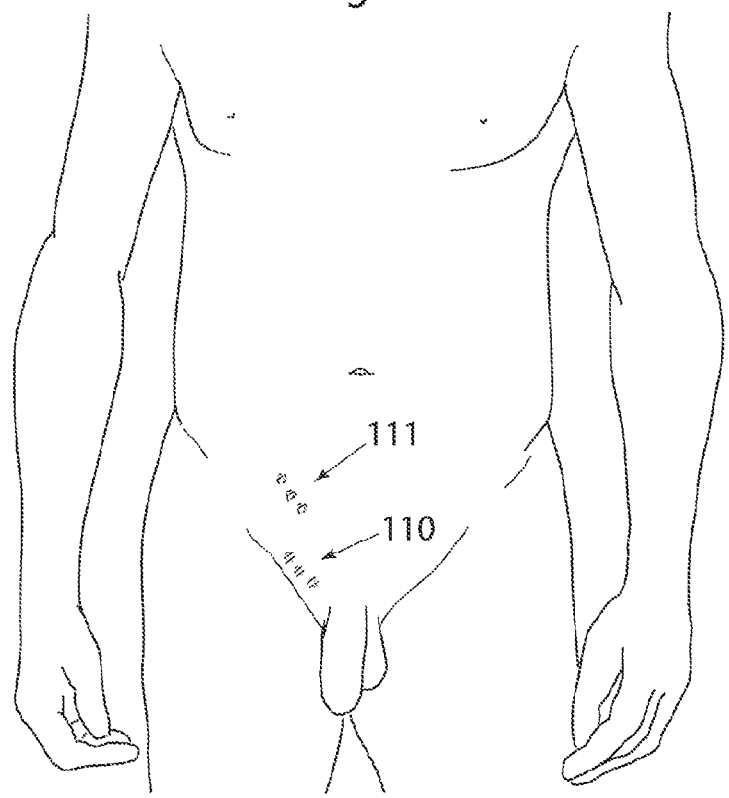

FIG. 21a shows the step of suturing 111 or stapling 110 the incisions made in the surgical method, whereas FIG. 21b shows the suturing 111 or stapling of the small incisions made in the laparoscopic/arthroscopic method.

Please note that any embodiment or part of embodiment as well as any method or part of method could be combined in any way. All examples herein should be seen as part of the general description and therefore possible to combine in any way in general terms.

The invention claimed is:

1. A medical device for delivering an action to an area of a hip joint or its surroundings, inside a human body of a patient, the hip joint comprising a collum femur and a ball shaped caput femur, being the proximal parts of the femoral bone, and an acetabulum, being a bowl shaped part of the pelvic bone, said medical device comprising;
  an elongated member, having a length axis along its elongated distribution, and a first portion having an end being adapted to enter the body of the patient, said first portion of said elongated member having a first portion cross-section area substantially perpendicular to the length axis of the elongated member, said first portion is adapted to pass through a hole in a bone of the patient, the hole having a hole cross-section area, wherein said first portion cross-section area is smaller than said hole cross-section area, the first portion comprising:
    i. a mounting portion, and
    ii. a holding member adapted to hold a mechanical element inside the body of said patient, and
  a mechanical element having a functional status ready to deliver an action inside the body when held by said holding member inside the body of the patient, wherein said mechanical element has a mechanical element cross-section area substantially perpendicular to the length axis of the elongated member, being substantially larger than said first portion cross-section area and unable to pass through the holes when said mechanical element is in said functional status, wherein the mechanical element comprises at least one mounting recess for mounting the mechanical element onto the mounting portion of the elongated member in a direction substantially perpendicular to the elongated member, wherein said elongated member has a maximum diameter in a central portion, and the mounting recess has a width corresponding to said maximum diameter such that a user of the medical device can mount the mechanical element on the central portion of the elongated member without having access to the end of the first portion of the elongated member.

2. The medical device according to claim 1, wherein said mechanical element cross-sectional area is in the interval 1.2-2 times larger than said first portion cross-sectional area or more than 2 times larger than said first portion cross-sectional area.

3. The medical device according to claim 1, wherein the first portion of the elongated member is long enough to at least one of;
  a. pass through a hole in the femoral bone, through the hip joint and through a hole in the pelvic bone entering the abdominal cavity, and
  b. pass through a hole in the femoral bone, through the hip joint and through a hole in the pelvic bone, entering the abdominal cavity and through the pelvic bone on the opposite side and further out through the skin of the patient, or the opposite direction through the skin of the patient, through the pelvic bone, through the abdominal cavity, through the pelvic bone on the opposite side, and into the hip joint.

4. The medical device according to claim 1, wherein said holding member is adapted to transfer a force from said elongated member to said mechanical element, for delivering said action during the operation, wherein said mechanical element is a tool adapted to deliver said action during said operation of said hip joint.

5. The medical device according to claim 1, wherein said mechanical element comprises at least one drilling tool.

6. The medical device according to claim 5, wherein said drilling tool is adapted to at least one of;
  a. create a hole in the pelvic bone by creating a bone plug, and
  b. create a hole in the pelvic bone from the abdominal side of the pelvic bone.

7. The medical device according to claim 1, wherein said mechanical element comprises at least one reaming tool adapted to ream at least one of the acetabulum and the caput femur of the human patient.

8. The medical device according to claim 1, wherein said mechanical element is a tool for fixating a fixation element to the area of the hip joint, wherein said fixation element comprises at least one fixation element selected from a group consisting of:
  a. at least one screw,
  b. at least one pin,
  c. at least one portion of at least one of the parts adapted to be introduced into the other part,
  d. the parts being adapted to be sliding into the other part,
  e. form fitting,
  f. welding,
  g. adhesive,
  h. bone cement
  i. pin,
  j. wire,
  k. a ball mounted into a bowl being portions of said parts,
  l. a male portion of one part mounted into a female portion of the other part,
  m. a key introduced into a lock being portions of said parts,
  n. band, and
  o. other mechanical connecting members.

9. The medical device according to claim 1, wherein said mechanical element comprises at least one fluid injecting tool, wherein said fluid injecting tool is adapted to inject at least one of; adhesive, bone cement, and a lubricating fluid.

10. The medical device according to claim 4, wherein said mechanical element is a tool for manipulating an implantable device comprising at least one of;
  an artificial acetabulum or an artificial acetabulum surface, and wherein said holding member is adapted to at least one of; hold said artificial acetabulum or said artificial acetabulum surface, for delivering the action to mount the artificial acetabulum or the artificial acetabulum surface in the hip joint, during said operation, and to center and hold said artificial acetabulum or an artificial acetabulum surface during fixation thereof in said hip joint, an artificial caput femur or an artificial caput femur surface, and wherein said holding member is adapted to at least one of; hold the artificial caput femur or the artificial caput femur surface, for delivering the action to mount the artificial caput femur or the artificial caput femur surface in the hip joint, during said operation, and to center and hold said artificial caput femur or said artificial caput femur during fixation thereof in said hip joint, and an intermediate part adapted to be placed between the acetabulum, or an artificial replacement therefore, and the caput femur, or an artificial replacement therefore.

11. The medical device according to claim 1, wherein said elongated member is at least one of;
   adapted for rotational movement,
   adapted for reciprocating movement,
   adapted for oscillating movement,
   comprising a rod,
   comprising a wire,
   comprising a part or section adapted to be bent.

12. The medical device according to claim 1, further comprising an operation device comprising at least one of; a motor and an adaptation for manual manipulation, the operation device adapted to;
   create force,
   connect to said elongated member,
   connect to said elongated member in at least one of the following positions; in the abdomen of the body, outside the body lateral of the proximal femoral bone, and
   outside the body, lateral on the opposite side of said hip joint of said body outside the ilium pelvic bone.

13. The medical device according to claim 1, wherein the elongated member is adapted to at least one of;
   be introduced into at least one of; the femoral bone, the pelvic bone, and an artificial hip joint surface,
   guide said artificial hip joint surface to a correct position inside the human body when said elongated member is introduced into a hole in an artificial hip joint surface,
   be fixated or stabilized to at least one of the femoral bone and the pelvic bone during, when an artificial hip joint surface is placed inside the human body,
   be removed from at least one of; the femoral bone, the pelvic bone, and an artificial hip joint surface, when an artificial hip joint surface has been placed inside the hip joint,
   have a first and second state, wherein in said first state said elongated member is flexible, and wherein in said second state said elongated member is adapted to be less flexible than in said first state,
   guide an artificial hip joint surface in at least one of; one, two, three axis, and in at least one plane,
   be placed in a positioning hole of at least one of; an artificial hip joint surface, and at least one of at least two artificial hip joint surface parts when an artificial hip joint surface comprises at least two artificial hip joint surface parts,
   be positioned in a positioning hole, being at least one of; substantially circular in an area substantially perpendicular to its elongated distribution, substantially non-circular in an area substantially perpendicular to its elongated distribution, and a hole having a cut circumference, and
   be supported in at least a first and a second supporting points, wherein at least one of; said first and said second supporting point are separated from each other, said first supporting point is a supporting point in the femoral bone, and wherein said second supporting point is a supporting point in the pelvic bone,
   control the placing of at least one prosthetic part in said hip joint,
   receive force from an operation device in at least one of: the abdomen, a position outside the body, lateral of the proximal femoral bone, and a position outside the body, lateral on the opposite side of the hip joint, outside the ilium pelvic bone on the opposite side of the hip joint, and
   receiving said artificial hip joint surface inserted into the hip joint through at least one of; the hip joint capsule and the pelvic bone, to be mounted onto said elongated member inside of the hip joint.

14. The medical device according to claim 1, wherein said elongated member is adapted for rotational movement.

15. The medical device according to claim 1, wherein said elongated member is adapted for reciprocating movement.

16. The medical device according to claim 1, wherein said elongated member is adapted for oscillating movement.

17. The medical device according to claim 1, wherein said elongated member comprises a wire.

18. The medical device according to claim 1, wherein said elongated member comprises a part or section adapted to be bent.

19. The medical device according to claim 1, wherein said elongated member is adapted to be supported in at least a first and a second supporting points, wherein said first and said second supporting point are separated from each other.

20. A medical device for delivering an action to an area of a hip joint or its surroundings, inside a human body of a patient, the hip joint comprising a collum femur and a ball shaped caput femur, being the proximal parts of the femoral bone, and an acetabulum, being a bowl shaped part of the pelvic bone, said medical device comprising;
   a. an elongated member, having a length axis along its elongated distribution, and a first portion having an end being adapted to enter the body of the patient, said first portion of said elongated member having a first portion cross-section area substantially perpendicular to the length axis of the elongated member, said first portion is adapted to pass through a hole in a bone of the patient, the hole having a hole cross-section area, wherein said first portion cross-section area is smaller than said hole cross-section area, the first portion comprising:
      iii. a mounting portion, and
      iv. a holding member adapted to hold a mechanical element inside the body of said patient, and
   b. a mechanical element having a functional status ready to deliver an action inside the body when held by said holding member inside the body of the patient, wherein said mechanical element has a mechanical element cross-section area substantially perpendicular to the length axis of the elongated member, being substantially larger than said first portion cross-section area and unable to pass through the holes when said mechanical element is in said functional status, wherein the mechanical element comprises at least one mounting recess for mounting the mechanical element onto the mounting portion of the elongated member in a direction substantially perpendicular to the elongated member, wherein said at least one mounting portion of the elongated member has a cross-sectional form, in a plane parallel to the length axis of the elongated member, and the mounting recess has a complementary cross-sectional form, wherein said cross-sectional form and complementary cross-sectional form each has at least two different widths.

* * * * *